(12) United States Patent
Burnam

(10) Patent No.: US 10,933,087 B2
(45) Date of Patent: *Mar. 2, 2021

(54) METHODS AND COMPOSITIONS FOR EYE CARE

(71) Applicant: GLOBAL HEALTH SOLUTIONS LLC, Rome, GA (US)

(72) Inventor: Bradley Burnam, Calabasas, CA (US)

(73) Assignee: GLOBAL HEALTH SOLUTIONS, LLC, Rome, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/582,998

(22) Filed: Sep. 25, 2019

(65) Prior Publication Data

US 2020/0093854 A1 Mar. 26, 2020

Related U.S. Application Data

(60) Provisional application No. 62/736,372, filed on Sep. 25, 2018, provisional application No. 62/742,841, filed on Oct. 8, 2018.

(51) Int. Cl.

| | |
|---|---|
| *A61K 31/785* | (2006.01) |
| *A61K 47/06* | (2006.01) |
| *A61K 9/08* | (2006.01) |
| *A61K 47/02* | (2006.01) |
| *A61P 27/02* | (2006.01) |
| *A61K 31/52* | (2006.01) |
| *A61K 9/00* | (2006.01) |
| *A61P 31/22* | (2006.01) |
| *A61K 31/522* | (2006.01) |

(52) U.S. Cl.
CPC .......... *A61K 31/785* (2013.01); *A61K 9/0048* (2013.01); *A61K 9/08* (2013.01); *A61K 31/52* (2013.01); *A61K 31/522* (2013.01); *A61K 47/02* (2013.01); *A61K 47/06* (2013.01); *A61P 27/02* (2018.01); *A61P 31/22* (2018.01)

(58) Field of Classification Search
CPC .......................... A61K 31/155; A61K 31/785
See application file for complete search history.

(56) References Cited

U.S. PATENT DOCUMENTS

2016/0367504 A1* 12/2016 Burnam .................. A61K 9/06
2019/0038750 A1* 2/2019 Selner .................. A61K 9/0014

OTHER PUBLICATIONS

Miserocchi et al. Am J Ophthalmol, 2007, 144(4): 547-51 (abstract).*

* cited by examiner

*Primary Examiner* — Rei Tsang Shiao
(74) *Attorney, Agent, or Firm* — Polsinelli PC

(57) ABSTRACT

Compositions and methods for the treatment or prevention of an ocular disease in an eye of a patient. The petrolatum-based compositions may include petrolatum and a saline solution comprising at least one cationic biocide. In at least some instances, the compositions do not require the use of an added emulsifier and may contain at least one antiviral agent. Methods of using the petrolatum-based compositions in the treatment of ocular diseases, including infections of the eye are provided. Additionally, processes for preparing such compositions are provided.

14 Claims, 2 Drawing Sheets

FIG. 3

METHODS AND COMPOSITIONS FOR EYE CARE

CROSS-REFERENCE TO RELATED APPLICATIONS

This application claims the benefit of U.S. Provisional Application Ser. No. 62/736,372, entitled "Methods and Compositions for Eye Care," filed Sep. 25, 2018, and 62/742,841, entitled "Methods and Compositions for Eye Care," filed Oct. 8, 2018, the contents of which are incorporated by reference herein, for all purposes, in their entirety.

FIELD

The present disclosure is broadly concerned with petrolatum-based compositions for eye care. The disclosure is also concerned with petrolatum-based compositions having cationic biocides and/or antiviral agents for the treatment and prevention of eye infections, including, but not limited to, herpes zoster opthalmicus (HZO) or shingles of the eye and viral conjunctivitis.

BACKGROUND

Infectious ocular disease and its complications are a significant health problem worldwide and may greatly impact quality of life. In particular, ocular infections by infectious agents such as bacteria, viruses, and fungi are responsible for a wide number of inflammatory disorders of the eye, including conjunctivitis, keratitis, blepharitis, vitritis, uveitis, chorioretinitis, and neuroretinitis. Ocular infections may cause blurred vision, itching, burning, discharge, and in some instances blindness. Trachoma, a contagious bacterial infection of the eye, is a leading cause of blindness in developing regions. Herpes zoster opthalmicus (HZO) is an ocular infection associated with Shingles that may result in sight threatening complications. HZO often occurs in older adults but can present at any age, typically occurring after reactivation of latent varicella-zoster virus (VZV) present within the sensory spinal or cerebral ganglia.

Keratitis is a condition in which the eye's cornea becomes inflamed. Infectious keratitis may be caused by bacteria, viruses, fungi, or amoebae. Viral keratitis is often caused by the herpes simplex virus and is frequently responsible for dendritic corneal ulcers. Bacterial keratitis is often caused by infection by *Staphylococcus aureus* or *Pseudomonas aeruginosa*. Acanthamoebic keratitis is a serious corneal infection that especially affects contact lens wearers and is caused by the amoeba *Acanthamoeba* potentially resulting in visual impairment or blindness if not effectively treated.

Among the most common infectious ocular diseases is infectious conjunctivitis which is generally caused by the presence of bacteria or viruses. Bacterial conjunctivitis may be caused by a variety of bacteria, such as *S. pneumoniae, H. influenza, P. aeruginosa*, or *S. pyogenes*. Subjects having bacterial conjunctivitis are typically treated with topical antibiotics.

Viral conjunctivitis may be caused by a variety of viruses, including adenovirus, herpes simplex virus (HSV), varicella-zoster virus (VZV), picornavirus (enterovirus 70, Coxsackie A24), poxvirus (molluscum contagiosum, vaccinia), and human immunodeficiency virus (HIV). Adenoviral conjunctivitis is the most common infectious agent responsible for viral conjunctivitis. Subtypes of adenoviral conjunctivitis include epidemic keratoconjunctivitis (pink eye) and pharyngoconjunctival fever. Primary ocular herpes simplex infection is also common, particularly in children, and is normally associated with a follicular conjunctivitis.

Successful treatment of infectious conjunctivitis is often limited by accurate diagnosis and differentiation of bacterial conjunctivitis versus viral conjunctivitis. Commonly, antibiotic drops are prescribed for patients having viral conjunctivitis when they are not needed or effective. Additionally, current antibiotic drops or ointments often cause irritation, burning of the eyes, and temporary blurred vision. Additional compositions and methods for the treatment of infectious ocular diseases are desirable. In particular compositions and methods that that are effective in treating both bacterial and viral infections of the eye and that are well-tolerated by the eye or do not cause eye irritation are desirable.

Cationic biocides are a group of antimicrobial compounds that have been in use for surface disinfection and topical applications for the treatment of infection. Cationic biocides are a diverse group of chemical compounds. Typically the antimicrobial action of cationic biocides stems from interaction of the cationic biocide with a microbe's cell envelope. The cationic biocide displaces divalent cations in the cell envelope, which ultimately results in membrane disruption that is lethal to the microbe. Additionally, cationic biocides are effective against certain viruses.

Petrolatum is known to have advantageous properties when applied to the eyes, such as being well-tolerated, capable of reducing irritation, and eye protection capabilities. However, formulating cationic biocides for topical administration to eyes using a petrolatum-based carrier, is complicated by the chemical structure of cationic biocides as well as the chemical nature of aqueous solutions suitable for eye formulations. Cationic biocides are charged, making them highly polar compounds. Therefore, the hydrophobic nature of petrolatum had previously made it a poor candidate for formulating cationic biocides because of their polar and hydrophilic structure. It was previously thought that an emulsifier would be necessary to disperse a cationic biocide throughout petrolatum. It was also thought that the petrolatum was incapable of delivering compounds such as cationic biocides because the cationic biocide would be trapped within the petrolatum and therefore would be unable to reach and interact with the infectious agent. Accordingly, petrolatum-based compositions comprising cationic biocides suitable for the treatment of ocular infections and other eye care applications are desirable. Additionally, compositions that contain cationic biocides and other antiviral agents that provide any one of greater patient comfort, tolerance, antiviral agent retention, and antiviral activity are desirable.

BRIEF DESCRIPTION OF THE FIGURES

The application file contains at least one photograph executed in color. Copies of this patent application publication with color photographs will be provided by the Office upon request and payment of the necessary fee.

FIG. 3 depicts a graph showing decrease of varicella zoster virus (VSV) expression for group 2 (treatment group)

Figure 1:
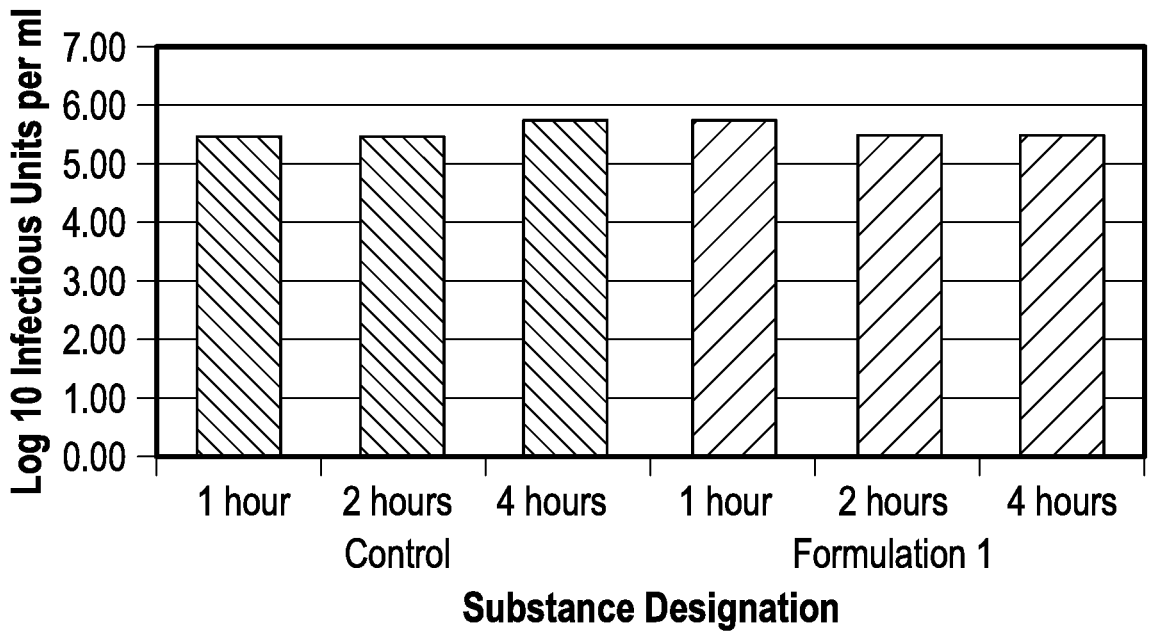
FIG. 1 depicts a graph showing the reduction of active Human Adenovirus 1 in suspension after 4 hours following exposure to Formulation 1 disclosed in Example 1, according to an exemplary embodiment of the present disclosure.

as compared to group 1 (control) after seven days of administration of Formulation 1 disclosed in Example 1 according to the protocol described in Example 12, according to an exemplary embodiment of the present disclosure.

DETAILED DESCRIPTION

The disclosure provides for petrolatum-based compositions comprising a saline solution that includes cationic biocides, processes for making petrolatum-based compositions having saline solutions comprising cationic biocides, and applications and uses of petrolatum-based compositions of comprising a saline solution that includes cationic biocides in the treatment and prevention of eye disease, including eye infections. Cationic biocides are polar active ingredients. The cationic biocides surprisingly may be dispersed throughout the petrolatum as nanodroplets with the petrolatum serving as a suspension matrix for the polar ingredients and saline solution carrier. Importantly, petrolatum-based compositions of the present disclosure generally do not contain an emulsifier. As it was discovered by the inventors, not only were emulsifiers not necessary for dispersing the cationic biocides and saline solution carrier in the petrolatum, but the structure of the compositions is shelf stable for extended periods of time even under non-ideal conditions. In addition, the compositions exhibit exceptional chemical stability of the cationic biocides, and are capable of delivering an active ingredient over extended periods of time. The novel formulations provide broad spectrum activity against microbes and certain viruses, are exceptionally gentle, and provide long-lasting antimicrobial activity, making the formulations particularly suitable for eye care applications. The presently disclosed petrolatum-based compositions comprising one or more cationic biocides, such as polihexanide biguanide (PHMB), in a petrolatum carrier without an emulsifier, exhibit advantages in delivering cationic biocides to the eye as compared to liquid cationic biocide formulations due to the gentle nature and extended wear capabilities of petrolatum and the lack of an emulsifier that may otherwise mask the therapeutic effectiveness of the cationic biocides and other therapeutic agents.

The Applicant has discovered that cationic biocides in a saline solution carrier can be formulated in petrolatum. The petrolatum-based compositions described herein contain nanodroplets of saline solution comprising cationic biocides dispersed in the petrolatum. The nanodroplets release the cationic biocides to the application site continuously and have been shown to provide broad spectrum activity against microbes and certain viruses. Additionally, the petrolatum-based compositions described herein are gentle. They do not irritate the eye and are not cytotoxic to mammalian cells.

It has further been discovered that an antiviral agent may be formulated in the presently disclosed petrolatum-based compositions. The antiviral agent may be, for example, acyclovir, valacyclovir, famciclovir, or any combination thereof. The antiviral agent may be comprise from about 0.5 wt % to about 5.0 wt % of the petrolatum-based composition, or from about 1.0 wt % to about 2.5 wt %, or from about 2.5 wt % to about 5.0 wt %, or from about 0.5 wt % to about 1.5 wt % of the petrolatum-based composition. The presently disclosed compositions have been found to advantageously deliver antiviral agents to the eye or ocular region of a patient with reduced eye irritation and increased patient comfort and tolerance as compared to other antiviral agent formulations. Additionally, the presently disclosed compositions provide for greater retention of the antiviral agents at the target site (e.g., the eye or ocular region of a patient) and enhanced antiviral activity and/or bioavailability of the antiviral agent at the target site.

I. Compositions

The disclosure provides for compositions that are petrolatum-based. A petrolatum-based composition is made up primarily of petrolatum. The characteristics of a petrolatum-based composition differ from a composition containing only a small amount of petrolatum. In some embodiments, the petrolatum-based composition is greater than about 80% petrolatum. In other embodiments, the petrolatum-based composition is greater than about 81% petrolatum, greater than about 82% petrolatum, greater than about 83% petrolatum, greater than about 84% petrolatum, greater than about 85% petrolatum, greater than about 86% petrolatum, greater than about 87% petrolatum, greater than about 88% petrolatum, greater than about 89% petrolatum, greater than about 90% petrolatum, greater than about 91% petrolatum, greater than about 92% petrolatum, greater than about 93% petrolatum, greater than about 94% petrolatum, greater than about 95% petrolatum, greater than about 96% petrolatum, greater than about 97% petrolatum, greater than about 98% petrolatum, or greater than about 99% petrolatum. The petrolatum is preferably medical grade petrolatum.

The compositions also contain one or more cationic biocides in a saline solution that is dispersed throughout the petrolatum. The cationic biocide is the composition ingredient active in killing microbes. Cationic biocides include quaternary ammonium compounds, bisbiguanides, and polymeric biguanides. The specific cationic biocides used in the invention include, but are not limited to, benzalkonium chloride, cetrimide, chlorhexidine, polihexanide biguanide (polihexanide, polyhexamethylene biguanide, polyhexamethylene guanide, poly(iminoimidocarbonyl-iminoimidocarbonyl-iminohexamethylene), poly(hexamethylenebiguanide), polyaminopropyl biguanide) and salts or combinations thereof. In one embodiment, the composition contains a mixture of polihexanide biguanide (PMHB) and benzalkonium chloride (BZK). The total amount of cationic biocide in the composition generally constitutes less than about 1% by weight of the total composition. In preferred embodiments, the cationic biocide constitutes from about 0.1% to about 1% by weight, or from about 0.1% to about 0.5% by weight, or from about 0.1% to about 0.3% by weight, or from about 0.2% to about 0.6% by weight, or from about 0.3% to about 0.5% by weight, to the total composition.

The remaining weight of the composition, typically from about 0.1% to about 6% by weight of the petrolatum-based composition, is a saline solution. In at least some instances, the composition contains about 5% saline solution. In some instances, the saline solution may be sodium chloride dissolved in water. The saline solution may be, for example, an aqueous 0.90% w/v sodium chloride solution. In other instances, the saline solution may be a solution chloride aqueous solution having from about 0.20% to about 1.2% w/v sodium chloride, or from about 0.40% to about 0.60% w/v sodium chloride, or from about 0.40% to about 0.95% w/v sodium chloride, or from about 0.30% to about 0.50% w/v sodium chloride, or from about 0.70% to about 1.1% w/v sodium chloride, or from about 0.75% to about 0.95% w/v sodium chloride.

In some instances, the saline solution may be a sodium chloride aqueous solution having from about 2 grams and about 12 grams, or from about 4 grams to about 6 grams, or from about 4 grams to about 9.5 grams, or from about 3 grams to about 5 grams, or from about 7 grams to about 1.1 grams, or from about 7.5 grams to about 9.5 grams sodium chloride per liter water.

The cationic biocides do not react with the petrolatum. Instead, the cationic biocide is dispersed in the petrolatum as nanodroplets, and the petrolatum serves as a suspension matrix for the cationic biocides. "Nanodroplet," as used herein, is an aggregation of cationic biocide molecules in the petrolatum base. The nanodroplets typically contain a small amount of water in addition to the cationic biocide. Nanodroplets in accordance with the invention are shown in FIG. 1. The nanodroplets may vary in size but generally the longest dimension of the nanodroplets measures from about 10 nm to about 10,000 nm. In various embodiments, the nanodroplets range from about 10 nm to about 100 nm, from about 100 nm to about 1000 nm, from about 1000 nm to about 2000 nm, from about 2000 nm to about 3000 nm, from about 3000 nm to about 4000 nm, from about 4000 nm to about 5000 nm, from about 5000 nm to about 6000 nm, from about 6000 nm to about 7000 nm, from about 7000 nm to about 8000 nm, from about 8000 nm to about 9000 nm, from about 9000 nm to about 10,000 nm. The nanodroplets are dispersed through the petrolatum homogeneously.

Surprisingly, embodiments of the present invention do not require an emulsifier. An emulsifier, as used herein, is an added formulation ingredient used to reduce the tension between hydrophilic and hydrophobic surface ingredients, thereby facilitating the mixture hydrophilic and hydrophobic ingredients. Prior to the present invention, those skilled in the art expected that an emulsifier would be needed to disperse cationic biocides and aqueous saline solutions, which are polar, in a non-polar petrolatum suspension matrix. Where an emulsifier is used, it has a hydrophilic-lipophilic balance (HLB) of less than 10.

The compositions described herein are stable. In one aspect, stability refers to the integrity of the composition as a whole, and in particular, the stability of the saline solution and cationic biocides in the petrolatum or the nanodroplets in the petrolatum. Under ambient conditions, the petrolatum and the cationic biocides/saline solution will not separate for greater than two years, meaning that the composition is shelf stable for at least two years. Even under accelerated conditions, such as reduced pressure, the petrolatum and the cationic biocides/saline solution do not separate, but rather the cationic biocides/saline solution remain suspended as in the petrolatum. In at least some instances, the cationic biocides/saline solution remain suspended as nanodroplets in the petrolatum. In addition to the stability of the cationic biocides/saline solution or nanodroplets within the composition, the compositions described herein also show exceptional chemical stability for the cationic biocide. The chemical stability stems primarily from the low-temperature manufacturing process described herein. The absence of excessive heat conditions in the manufacturing of the compositions improves the chemical stability (resistance to degradation) for the cationic biocides.

In some embodiments, the petrolatum-based compositions described herein consist essentially of petrolatum, a cationic biocide, and saline solution. In one preferred embodiment, the petrolatum-based compositions consist essentially of petrolatum, benzalkonium chloride, polihexanide biguanide, and saline solution. In alternative embodiments, the petrolatum-based compositions described herein consist of petrolatum, a cationic biocide, and saline solution or consist of petrolatum, benzalkonium chloride, polihexanide biguanide, and saline solution.

In other embodiments, the petrolatum-based compositions described herein may further comprise a compound that stimulates healing. More specifically, the petrolatum-based compositions described herein may further comprise a compound that stimulates healing for use in eye care. Non-limiting examples of compounds that stimulate healing include polycaprolactone-tricalcium phosphate (PCL-TCP), collagen, chitosan, cellulose, thrombin, chondroitin sulfate (CS), chondroitin sulfate succinimidyl succinate (CS-NHS), and growth factors such as TGF-alpha, TGF-beta (TGFβ1, TGFβ2, TGFβ3), platelet-derived growth factor (PDGF), epidermal growth factor (EGF), fibroblast growth factor also referred to as keratinocyte growth factor (FGF1, FGF2, FGF4, FGF7), vascular endothelial growth factor (VEGF), insulin-like growth factor (IGF), connective tissue growth factor (CTGF), activin, interleukin-1 (IL1α, IL1β), TNFα, GM-CSF, or autologous intraoperative biologics such as platelet-rich plasma (PRP) and bone marrow (BM).

Additionally, the compositions may be incorporated in predetermined therapeutically effective amounts into disposables suitable for eye care such as wipes, gauze, patches, wraps, bandages, adhesive strips, sponge, cotton swab, medication pad, tissue, pain-relief gel pack and the like. For instance, the composition may be applied to the surface of, or impregnated into disposables.

II. Process for Making

The disclosure also provides a method for making the compositions described in Section (I). The process comprises: (a) preparing a saline solution comprising water, sodium chloride, and at least one cationic biocide; (b) heating the petrolatum to a temperature sufficient to give a melted petrolatum, and heating the saline solution to a temperature higher than the temperature of the petrolatum to give a heated saline solution; (c) mixing the melted petrolatum and the heated saline solution to give a melted mixture; and, (d) cooling the melted mixture to give the petrolatum-based composition. As would be appreciated by one of skill in the art, steps (a)-(d) are conducted sequentially.

The cationic biocide, selected from the group described in Section (I), is first dissolved in an aqueous solution comprising a salt, such as sodium chloride, to form a saline solution comprising cationic biocide. The cationic biocide is typically dissolved in the saline solution at a concentration ranging from about 1% to about 15% by weight. In at least some instances, the cationic biocide is dissolved in the saline solution at a concentration of about 10% by weight, or from about 5% to about 12% by weight, or from about 9% to about 11% by weight. Typically, the amount of saline solution comprising cationic biocide used is from about 1:10 to about 1:30 the amount of petrolatum and more preferably is about 1:20 to the amount of petrolatum by volume. In at least some instances, the saline solution comprises from about 1% to about 10% by weight of the petrolatum-based composition. In other instances, the saline solution may comprise from about 2% to about 5%, or from about 3% to about 10%, or from about 4% to about 10%, or from about 5% to about 10%, or from about 1% to about 5%, by weight of the petrolatum-based composition. The amount of cationic biocide can be calculated by one skilled in the art to provide the desired weight percentage for the final composition. In some instances, the saline solution may include an antiviral agent. The antiviral agent may be, for example, acyclovir, valacyclovir, famciclovir, or any combination thereof.

Both the saline solution and the petrolatum are heated. The heating of these two ingredients can be conducted at the same time or sequentially so long as the melted petrolatum and the heated saline solution are at the appropriate temperatures during the mixing step. Petrolatum is a solid that melts at approximately 37° C. As such, petrolatum may be heated to any temperature at or above 37° C. For instance, the petrolatum may be heated to a temperature ranging from about 37° C. to about 45° C., from about 40° C. to about 50° C., from about 45° C. to about 55° C., from about 50° C. to about 60° C., from about 55° C. to about 65° C., from about 60° C. to about 70° C., from about 65° C. to about 75° C., from about 70° C. to about 80° C., from about 75° C. to about 85° C., from about 80° C. to about 90° C., from about 85° C. to about 95° C., or from about 90° C. to about 100° C. or more. Higher temperatures may also be envisioned. Preferably, the petrolatum is heated to a temperature ranging from about 37° C. to about 55° C., more preferably to a temperature ranging from about 40° C. to about 50° C. Heat may be provided to the petrolatum by any method known in the art, but a water bath or low temperature hot plate are preferred.

The saline solution is heated to a temperature above the temperature of the melted petrolatum. Any temperature above the temperature of the melted petrolatum may be used in a method of the present disclosure, provided that the heat does not cause excessive degradation of an active ingredient such as a cationic biocide, or excessive evaporation of the active ingredient or saline solution. For instance, the saline solution may be heated to a temperature that is about 1° C. to about 10° C., about 5° C. to about 15° C., about 10° C. to about 20° C., about 15° C. to about 25° C., about 20° C. to about 30° C., about 25° C. to about 35° C., about 30° C. to about 40° C., about 35° C. to about 45° C., about 40° C. to about 50° C., about 45° C. to about 55° C., about 50° C. to about 60° C. or about 65° C. or about 75° C. higher than the temperature of the melted petrolatum. Higher temperatures may also be envisioned. Preferably, the saline solution is heated to a temperature that is about 1° C. to about 10° C. higher than the temperature of the melted petrolatum. In another embodiment, the saline solution is heated to a temperature that is about 1° C. to about 5° C. higher than the melted petrolatum. In still other embodiments, the saline solution is heated to a temperature that is about 1° C., 2° C., 3° C., 4° C., or 5° C. above the temperature of the melted petrolatum. Again, the heating can be provided by any means known in the art but is preferably provided by a water bath or low temperature hot plate.

Once both the petrolatum and the saline solution are heated as described above, the melted petrolatum and the heated saline solution are mixed to give a melted mixture containing petrolatum and the heated saline solution. The mixing can be accomplished by a variety of methods including homogenization, acoustic mixing, and high RPM mixing. Depending on the batch size, the size of the mixer, and the type of mixing, the mixing may be conducted for several minutes or more. When mixed in accordance with the parameters disclosed above, the melted petrolatum and the heated saline solution fuse in the melted mixture.

After the melted petrolatum and the heated saline solution have fused they are allowed to cool and solidify into the composition described more fully in Section (I) ("the final composition"). Cooling may be achieved by reducing the amount of heat provided to the melted mixture, or cooling may be achieved passively under conditions where no heating is added. In some embodiments, cooling is controlled so that the temperature of the melting mixture is gradually lowered to ambient temperatures. The product is preferably packaged a few degrees above its solidification point so that the packaging can be filled by pouring the melted mixture. The composition preferably solidifies to the final composition in the package. The package is sealed after this solidification.

The process may be conducted with two or more cationic biocides. The cationic biocides may be dissolved in separate saline solutions or may be dissolved in the same saline solution. Addition of additional cationic biocides does not change the process steps above.

In at least some instances, the compositions may include one or more antiviral agents. The antiviral agent may be, for example, acyclovir, valacyclovir, famciclovir, or any combination thereof. In some instances, the antiviral agent may be added to the saline solution prior to heating and mixing with the petrolatum. In other instances, the antiviral agent may be added directly to the heated petrolatum prior to mixing with the heated saline solution. In still other cases, the antiviral agent may be added to the final petrolatum-based composition either while still warm or cooled.

III. Methods of Use

In another aspect, the invention encompasses a method of preventing or treating ocular diseases or eye infections using the composition described herein.

The compositions may be applied topically to the eye of a subject in need. Subjects in need may be those with an ocular disease, such as an eye infection. Subjects in need may also be subjects at risk for an ocular disease or an eye infection. The subject is preferably human but the composition may also be useful in animals, for example domestic animals, livestock, or other types of animals. Typically, the composition is applied to the eye of the subject.

The composition may be used in to kill a variety of microbes responsible for eye infections and ocular diseases. Exemplary microbes include *Aspergillus, Staphylococcus, Streptococcus, Peptostreptococcus, Corynebacterium, Clostridium, Listeria, Bacillus, Enterobacteriaceae, Pseudomonas, Moraxella, Helicobacter, Stenotrophomonas, Bdellovibrio, Legionella, Candida,* and *Trychophyton*. Exemplary microbes include *Staphylococcus aureus*, Methicillin-resistant *Staphylococcus aureus* (MRSA), *Pseudomonas aeruginosa, Escherichia coli, Candida albicans, Aspergillus niger, Trichophyton rubrum, S. pneumoniae, H. influenza,* and *S. pyogenes*.

The composition when applied to the eye is non-irritating and non-cytotoxic. These properties allow the composition to be used on sensitive eyes. These characteristics also allow for use to treat or prevent infections over a long period, such as for example 2 weeks, 4 weeks, 6 weeks, 8 weeks, or longer without irritation to the treated area. It will be recognized however, that the compositions may be used for shorter periods of time if necessary.

The compositions are also capable of extended release of the cationic biocide to the area of application. "Extended release" as used herein means that the compositions release cationic biocides to the application site over a period of time extending past twelve hours. The time over which the extended release is provided is variable depending on the amount of the composition that is applied and on the heat of the tissue, but in general, the release of cationic biocides is extended beyond the initial application and cationic biocides have been shown to be released for up to 1 week. This extended release allows the composition to be applied less frequently and improves patient compliance with the treatment.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1. Exemplary Formulation Process

"Formulation 1" was prepared by mixing 49.8375 g of 0.9% w/v NaCl saline solution with 50.0 g of a 20% polihexanide biguanide, also known as poly(hexamethylenebiguanide) hydrochloride (PHMB), solution (Cosmocil CQ), and 0.1625 g of a 80% benzalkonium chloride, also known as n-alkyl dimethylbenzyl ammonium chloride (BZK), solution (Maquat MC1412-80E) to form a saline solution comprising the cationic biocides PHMB and BZK. The resultant prepared saline solution comprising cationic biocides contained approximately 0.49% w/v NaCl (4.92 grams NaCl per 1000 mL H$_2$O), 10% PHMB, and 0.13% BZK. Approximately 100 grams of saline solution comprising cationic biocides was heated to 122° F. and slowly added to approximately 1900 grams petrolatum heated to a temperature of 113° F. The heat was decreased slowly to between about 96° F. to about 104° F.

The resulting composition was shiny and white to slightly yellow in appearance. Specific gravity at 25° C. matches specification when it is from 0.830-0.910. Viscosity at @ 25° C. TF @ 10 rpm matches specification when it is from about 225,000-300,000 cps. The final formulation contained the following ingredients by weight percent: 95% petrolatum, 0.5% PHMP, 0.0065% BZK, and 4.49% saline solution.

Example 2. Antiviral Activity and Efficacy of Formulation of Example 1

A study was conducted on the formulation of Example 1, referred to herein as "Formulation 1" to assess antiviral activity and efficacy. ASTM International Standard Test Method E1052 was used to assess the effectiveness of the Formulation 1 against viruses in suspension. In the ASTM E1052 test, a suspension of virus was exposed to the composition of Formulation 1 at a ratio of 1:10 (1 part virus suspension+9 parts Formulation 1). A control suspension was concurrently processed in the same manner, with cell culture medium employed in place of the test product. Following neutralization, the suspensions were enumerated using standard cell culture (e.g., TCID$_{50}$) or plaque assay techniques. Log$_{10}$ and percent reduction values were calculated to determine the effectiveness of the test product suspension relative to the control suspension.

The viruses selected for the tests were Human Adenovirus 1 (ATCC VR-1) and Herpes Simplex Virus 1 (HSV-1) (ATCC VR-260). Human Adenovirus 1 is a relatively large, non-enveloped, double-stranded DNA member of the Adenoviridae family that was first isolated from human adenoid tissue. Adenoviruses are often responsible for viral conjunctivitis. Adenovirus 1 is understood to be highly stable and capable of surviving outside of a host on common environmental surfaces for extended periods of time. Because Human Adenovirus 1 is extremely hardy when deposited on environmental surfaces, it can be relatively difficult to inactivate via disinfection. The permissive host cell line for Adenovirus 1 was MRC-5 (Human Lung Fibroblast Cells), ATCC CCL-171.

Herpes Simplex Virus 1 (HSV-1) is an enveloped, double-stranded DNA virus of the genus Simplexvirus. Ocular HSV-1 is also commonly responsible for viral conjunctivitis in the eye. HSV-1 is common world-wide and it is estimated that the majority of United States citizens are exposed to or infected by HSV-1 by the time they reach adolescence. The permissive host cell line for HSV-1 was Vero (African Green Monkey Kidney Cells), ATCC CCL-81.

Viral and cytotoxicity titers (TCID$_{50}$/TCLD$_{50}$ and TCCD$_{50}$, respectively) were determined according to the method developed by Spearman-Karber:

$$-\log_{10} \text{ of 1st Dilution} - \left(\frac{\text{sum of \% mortality at each dilution}}{100}\right) - 0.5$$

Figure 2:
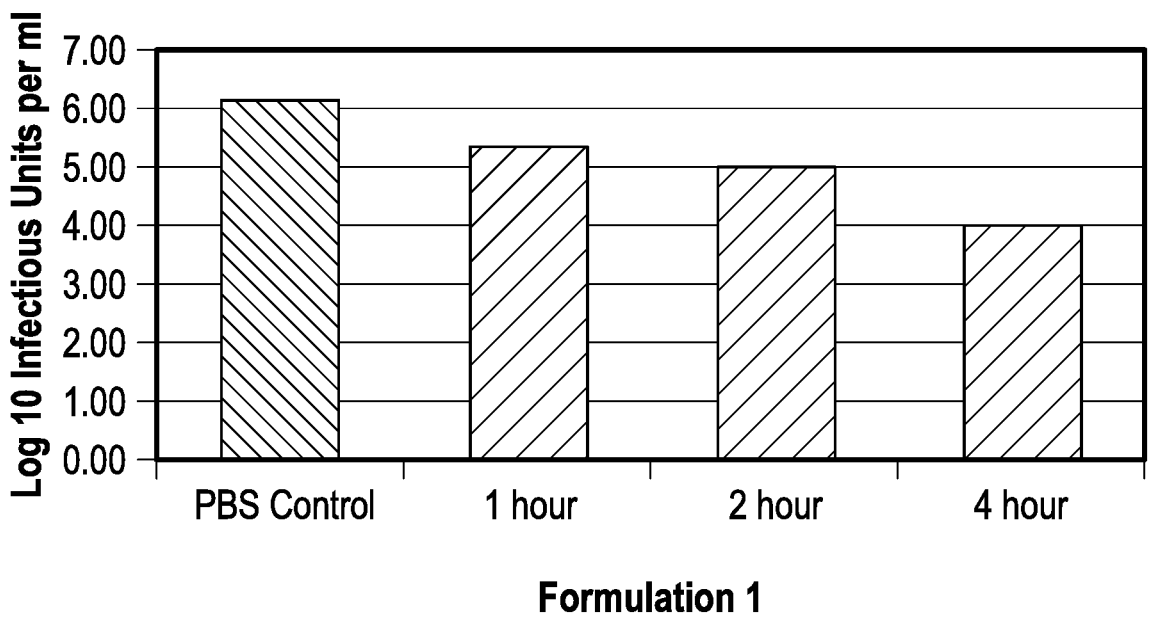
FIG. 2 depicts a graph showing the reduction of active Herpes Simplex Virus 1 (HSV-1) in suspension following exposure to Formulation 1 disclosed in Example 1, according to an exemplary embodiment of the present disclosure.

Percent reduction of virus was determined according to the following formula:

$$\text{Percent Reduction} = 1 - \left(\frac{C}{B}\right) \times 100,$$

where C is the Log$_{10}$ of the virus test carrier and B is the Log$_{10}$ of the virus control carrier. Phosphate-buffered saline (PBS) was used as a control. Table 1 and FIG. 1 provides the test results for Human Adenovirus 1 while Table 2 and FIG. 2 shows the test results for Herpes Simplex Virus I (HSV-1). As shown in Table 1 and FIG. 1, the composition of Formulation 1 was effective at inactivating Human Adenovirus 1 in suspension after 4 hours. Likewise, the results shown in Table 2 and FIG. 2 demonstrate that the composition of Formulation 1 was effective at inactivating Herpes Simplex Virus 1 (HSV-1) in suspension after 1 hour.

TABLE 1

Activity and Efficacy of Formulation 1 (Example 1) Against Human Adenovirus 1

| Virus | Substance Tested | Contact Time | Log$_{10}$ TCID$_{50}$ per mL | Log$_{10}$ Reduction Relative to Control | Percent Reduction Relative to Control |
|---|---|---|---|---|---|
| Human Adenovirus 1, ATCC VR-1 | PBS Control | 1 hour | 5.50 | N/A | |
| | | 2 hours | 5.50 | | |
| | | 4 hours | 5.75 | | |
| | Formulation 1 (Example 1) | 1 hour | 5.75 | No Reduction | No Reduction |
| | | 2 hours | 5.50 | No Reduction | No Reduction |
| | | 4 hours | 5.50 | 0.25 | 43.77% |

TABLE 2

Activity and Efficacy of Formulation 1 (Example 1) Against Herpes Simplex Virus 1 (HSV-1)

| Virus | Substance Tested | Contact Time | Log$_{10}$ Infectious Units per mL | Log$_{10}$ Reduction Relative to Control | Percent Reduction Relative to Control |
|---|---|---|---|---|---|
| Herpes Simplex 1, ATCC VR-260 | PBS Control | | 6.13 | N/A | |
| | Formulation 1 (Example 1) | 1 hour | 5.25 | 0.88 | 86.82% |
| | | 2 hours | 5.00 | 1.13 | 92.59% |
| | | 4 hours | 4.00 | 2.13 | 99.26% |

Example 3. Ocular Irritation Test of Formulation 1 of Example 1

Ocular irritation was determined using three healthy female nulliparous non-pregnant albino New Zealand White rabbits. The eyes of each rabbit were visually examined for evidence of ocular abnormality not more than 24 hours before test application. The rabbits were housed in a clean, dust free, temperature controlled environment that excludes materials that might produce eye irritation. The lower lid of the right eye of each rabbit was gently pulled away from the eyeball to form a cup and 0.1 mL of the composition of Formulation 1 (Example 1) was administered. The lids were gently held together for about one second. The left eye was left untreated and served as a control. The reaction was graded according to the system described in Table 3. Using the criteria outlined in Table 3, the cornea, iris, and conjunctivae of both eyes were examine at 1, 24, 48, and 72 hours after administration.

TABLE 3

System for Grading Ocular Irritation

| Reaction | Numerical Grading |
|---|---|
| 1. Cornea | |
| Degree of opacity (most dense area) | |
| No opacity | 0 |
| Scattered or diffuse area, details of iris clearly visible | 1* |
| Easily discernible translucent areas, details of the iris slightly obscured | 2* |
| Opalescent areas, no details of iris visible, size of pupil barely discernible | 3* |
| Opaque, detail of iris not visible | 4* |
| 2. Iris | |
| Normal | 0 |
| Folds above normal, congestion swelling, circumcorneal injection (any or all or combination of these), iris still reacting to light (sluggish reaction is positive) | 1* |
| No reaction to light, haemorrhage, gross destruction (any or all of these) | 2* |
| 3. Conjunctivae | |
| Redness (refers to palpebral and bulbar conjunctiva excluding cornea and iris) | |
| Vessels normal | 0 |
| Vessels definitely injected above normal | 1 |
| More diffuse, deeper crimson red, individual vessels not easily discernible | 2* |
| Diffuse beefy red | 3* |
| Chemosis | |
| No swelling | 0 |
| Any swelling above normal (include nictitating membrane) | 1 |
| Obvious swelling with partial eversion of lids | 2* |
| Swelling with lids about half-closed | 3* |
| Swelling with lids about half-closed to completely closed | 4* |

*Positive Result

Tables 4-7 provide the ocular irritation test results for the cornea, iris, conjunctivae, and chemosis, respectively. A score of ≥1 on the cornea and iris tests indicates a positive response while a score of ≥2 on the conjunctivae and chemosis tests indicates a positive results. As seen in Tables 4-7, Formulation 1 was non-irritating to and well-tolerated by the test subjects.

TABLE 4

Cornea Irritation Test Results for Formulation 1 (Example 1)

| | Rabbit # | | | | | |
|---|---|---|---|---|---|---|
| | 14997 | | 14996 | | 14998 | |
| | Test | Control | Test | Control | Test | Control |
| 1 Hour | 0 | 0 | 0 | 0 | 0 | 0 |
| 24 Hours | 0 | 0 | 0 | 0 | 0 | 0 |
| 48 Hours | 0 | 0 | 0 | 0 | 0 | 0 |
| 72 Hours | 0 | 0 | 0 | 0 | 0 | 0 |

TABLE 5

Iris Irritation Test Results for Formulation 1 (Example 1)

| | Rabbit # | | | | | |
|---|---|---|---|---|---|---|
| | 14997 | | 14996 | | 14998 | |
| | Test | Control | Test | Control | Test | Control |
| 1 Hour | 0 | 0 | 0 | 0 | 0 | 0 |
| 24 Hours | 0 | 0 | 0 | 0 | 0 | 0 |
| 48 Hours | 0 | 0 | 0 | 0 | 0 | 0 |
| 72 Hours | 0 | 0 | 0 | 0 | 0 | 0 |

TABLE 6

Conjunctivae Irritation Test Results for Formulation 1 (Example 1)

| | Rabbit # | | | | | |
|---|---|---|---|---|---|---|
| | 14997 | | 14996 | | 14998 | |
| | Test | Control | Test | Control | Test | Control |
| 1 Hour | 1 | 0 | 1 | 0 | 1 | 0 |
| 24 Hours | 0 | 0 | 0 | 0 | 0 | 0 |
| 48 Hours | 0 | 0 | 0 | 0 | 0 | 0 |
| 72 Hours | 0 | 0 | 0 | 0 | 0 | 0 |

TABLE 7

Chemosis Irritation Test Results for Formulation 1 (Example 1)

| | Rabbit # | | | | | |
|---|---|---|---|---|---|---|
| | 14997 | | 14996 | | 14998 | |
| | Test | Control | Test | Control | Test | Control |
| 1 Hour | 1 | 0 | 1 | 0 | 1 | 0 |
| 24 Hours | 0 | 0 | 0 | 0 | 0 | 0 |
| 48 Hours | 0 | 0 | 0 | 0 | 0 | 0 |
| 72 Hours | 0 | 0 | 0 | 0 | 0 | 0 |

Example 4. Cytotoxicity Evaluation of Formulation 1 of Example 1

The study was conducted to assess the biological reactivity of mammalian cells (grown in culture) to the agar-diffusible elements of Formulation 1.

The samples to be evaluated for cytotoxicity include test product comprising Formulation 1, Amber latex tubing as a positive control, and HDPE sheet stock as a negative control. Prior to exposure to the samples, the L929 Mouse Fibroblast cells were subcultured in Minimum Essential Medium (MEM) with 5% Fetal Bovine Serum (FBS) to achieve a confluency of approximately 80±10% at the time of exposure. The cells were examined for normal morphology and the absence of contamination. Once the cells met the acceptance criteria for use, individual dishes were numbered in triplicate to represent the controls and the test product comprising Formulation 1.

On the day of testing, the subculture media was carefully removed from the wells and replaced with an equivalent amount of Formulation 1. Exposure time and the date were identified on the plates used. Each of the test plates were then placed in the 37° C./5% $CO_2$ incubator to initiate the exposure interval. Microscopic readings for cellular response were performed at 24 hours and 72 hours after exposure. Table 8 provides the grading guidelines. A preliminary microscopic examination of the cells was made prior to staining and before the control and test product comprising Formulation 1 were removed from the agar layer. At least one well was stained with Trypan Blue at the final reading to help determine "percent lysed." Following staining, the cellular responses were then evaluated microscopically and macroscopically (by examining the dishes against a white surface) and the results were recorded.

TABLE 8

Grading Guidelines for Cytotoxicity Evaluation

| Grade | Reactivity | Conditions of Cell Cultures |
| --- | --- | --- |
| 0 | None | Discrete intracytoplasmic granules; no cell lysis. |
| 1 | Slight | No more than 20% of the cells are round, loosely attached and without intracytoplasmic granules; occasional lysed cells may be present. |
| 2 | Mild | Not more than 50% of the cells are round and devoid of intracytoplasmic granules; cell lysis and empty areas between cells may be present. |
| 3 | Moderate | Not more than 70% of the cell layers contain rounded cells and/or are lysed. |
| 4 | Severe | Nearly complete destruction of the cells' layers |

Table 9 provides the results of the cytotoxicity testing of the composition of Formulation 1. According to the USP guidance, grades of 0 (None), 1 (Slight), or 2 (Mild) indicate the tested composition meets the assay acceptance requirements for cytotoxicity. As shown in Table 9, Formulation 1 was found to meet the acceptance requirements for cytotoxicity and is considered to be non-cytotoxic.

TABLE 9

Cytotoxicity Test Results for Formulation 1 (Example 1)

|  | 24 Hours | | | 72 Hours | | | Trypan Blue % Lysed |
| --- | --- | --- | --- | --- | --- | --- | --- |
| Material Positive Control | 4 | 4 | 4 | 4 | 4 | 4 | 100% |
| Material Negative Control | 0 | 0 | 0 | 0 | 0 | 0 | 0% |
| Extract Negative Control | 0 | 0 | 0 | 0 | 0 | 0 | 0% |
| Test Article | 2 | 2 | 2 | 1 | 1 | 1 | 5% |

Example 5. Stability of Formulation 1 (Example 1)

Formulation 1 was packaged in tubes and subjected to an accelerated stability study. Formulation 1 was placed sideways in a 40° C.±2° C./75%±5% relative humidity (RH) storage chamber for different intervals to yield a period of three months. The composition was assessed for physical and analytical characteristics. When stored at 40° C.±2° C./75%±5% (RH) for three months the composition was observed to be stable (e.g., saline solution/cationic biocide did not separate from the petrolatum).

Example 6. Topical Administration of Formulation 1 to the Ocular Region Improves Clinical Outcomes in Subjects Having an Ocular Infection The effect of topical administration of the presently disclosed compositions to the ocular region of human subjects having an ocular infection will be studied using a randomized, double-blind clinical study. During the clinical study, a group of human subjects will be topically administered one of the presently disclosed compositions including, but not limited to, Formulation 1. In particular, the presently disclosed composition will be applied to the ocular region of a subject having or otherwise affected by the ocular infection. The subject may have an ocular infection as a result of a fungal infection, an amoeba infection, a viral infection, or a bacterial infection. Subjects receiving treatment using the presently disclosed compositions are expected to have improved standard clinical outcomes. In particular, subjects receiving treatment according to the presently disclosed methods and techniques are expected to exhibit an improvement in one or more of the following clinical outcomes: reduction in eye redness or irritation, reduction in pain or discomfort, reduction in duration of presentation of the ocular infection, reduction or mitigation of symptoms associated with ocular infections, reduction in blurred vision, and a reduction in discharge from the eye.

Example 7. Topical Administration of Formulation 1 to the Ocular Region Improves Clinical Outcomes in Subjects Having Infectious Conjunctivitis The effect of topical administration of the presently disclosed compositions to the ocular region of human subjects having infectious conjunctivitis will be studied using a randomized, double-blind clinical study. During the clinical study, a group of human subjects will be topically administered one of the presently disclosed compositions including, but not limited to, Formulation 1. In particular, the presently disclosed composition will be applied to the ocular region of a subject having or otherwise affected by the infectious conjunctivitis. The subject may have bacterial conjunctivitis or viral conjunctivitis. Subjects receiving treatment using the presently disclosed compositions are expected to have improved standard clinical outcomes. In particular, subjects receiving treatment according to the presently disclosed methods and techniques are expected to exhibit an improvement in one or more of the following clinical outcomes: reduction in eye redness or irritation, reduction in pain or discomfort, reduction in duration of presentation of conjunctivitis, reduction or mitigation of symptoms associated with conjunctivitis, reduction in blurred vision, and reduction in discharge from the eye.

Example 8. Topical Administration of Formulation 1 to the Ocular Region Improves Clinical Outcomes in Subjects Having Infectious Keratitis The effect of topical administration of the presently disclosed compositions to the ocular region of human subjects having infectious keratitis will be studied using a randomized, double-blind clinical study. During the clinical study, a group of human subjects will be topically administered one of the presently disclosed compositions including, but not limited to, Formulation 1. In particular, the presently disclosed composition will be applied to the ocular region of a subject having or otherwise affected by the infectious keratitis. The subject may have bacterial keratitis, viral keratitis, fungal keratitis, or acanthamoebic keratitis. Subjects receiving treatment using the presently disclosed compositions are expected to have improved standard clinical outcomes. In particular, subjects receiving treatment according to the presently disclosed methods and techniques are expected to exhibit an improvement in one or more of the following clinical outcomes: reduction in eye redness or irritation, reduction in pain or discomfort, reduction in duration of presentation of keratitis, reduction or mitigation of symptoms associated with keratitis, reduction in blurred vision, and reduction in discharge from the eye.

Example 9. Topical Administration of Formulation 1 to the Ocular Region Improves Clinical Outcomes in Subjects Having Ocular Histoplasmosis Syndrome The effect of topical administration of the presently disclosed compositions to the ocular region of human subjects having ocular histoplasmosis syndrome will be studied using a randomized, double-blind clinical study. During the clinical study, a group of human subjects will be topically administered one of the presently disclosed compositions including, but not limited to, Formulation 1. In particular, the presently disclosed composition will be applied to the ocular region of a subject having or otherwise affected by the ocular histoplasmosis syndrome. Subjects receiving treatment using the presently disclosed compositions are expected to have improved standard clinical outcomes. In particular, subjects receiving treatment according to the presently disclosed methods and techniques are expected to exhibit an improvement in one or more of the following clinical outcomes: reduction in eye redness or irritation, reduction in pain or discomfort, reduction in duration of presentation of ocular histoplasmosis syndrome, reduction or mitigation of symptoms associated with ocular histoplasmosis syndrome, reduction in blurred vision, and reduction in discharge from the eye.

Example 10. Topical Administration of Formulation 1 to the Ocular Region Improves Clinical Outcomes in Subjects Having Trachoma The effect of topical administration of the presently disclosed compositions to the ocular region of human subjects having trachoma will be studied using a randomized, double-blind clinical study. During the clinical study, a group of human subjects will be topically administered one of the presently disclosed compositions including, but not limited to, Formulation 1. In particular, the presently disclosed composition will be applied to the ocular region of a subject having or otherwise affected by the trachoma. Subjects receiving treatment using the presently disclosed compositions are expected to have improved standard clinical outcomes. In particular, subjects receiving treatment according to the presently disclosed methods and techniques are expected to exhibit an improvement in one or more of the following clinical outcomes: reduction in eye redness or irritation, reduction in pain or discomfort, reduction in duration of presentation of trachoma, reduction or mitigation of symptoms associated with trachoma, reduction in blurred vision, and reduction in discharge from the eye.

Example 11. Topical Administration of Formulation 1 to the Ocular Region Improves Clinical Outcomes in Subjects Having Herpes Zoster Opthalmicus (HZO)

The effect of topical administration of the presently disclosed compositions to the ocular region of human subjects having herpes zoster opthalmicus (HZO) will be studied using a randomized, double-blind clinical study. During the clinical study, a group of human subjects will be topically administered one of the presently disclosed compositions including, but not limited to, Formulation 1. In particular, the presently disclosed composition will be applied to the ocular region of a subject having or otherwise affected by the herpes zoster opthalmicus (HZO). Subjects receiving treatment using the presently disclosed compositions are expected to have improved standard clinical outcomes. In particular, subjects receiving treatment according to the presently disclosed methods and techniques are expected to exhibit an improvement in one or more of the following clinical outcomes: reduction in eye redness or irritation, reduction in pain or discomfort, reduction in duration of presentation of herpes zoster opthalmicus (HZO), reduction or mitigation of symptoms associated with herpes zoster opthalmicus (HZO), reduction in blurred vision, and reduction in discharge from the eye.

Example 12. In-Vivo Rodent Study Demonstrates Reduction in Expression of Varicella Zoster Virus (VSV) in the Eyes of Rodents Having Herpes Zoster Opthalmicus (HZO) Following Topical Administration of Formulation 1

Figure 3:
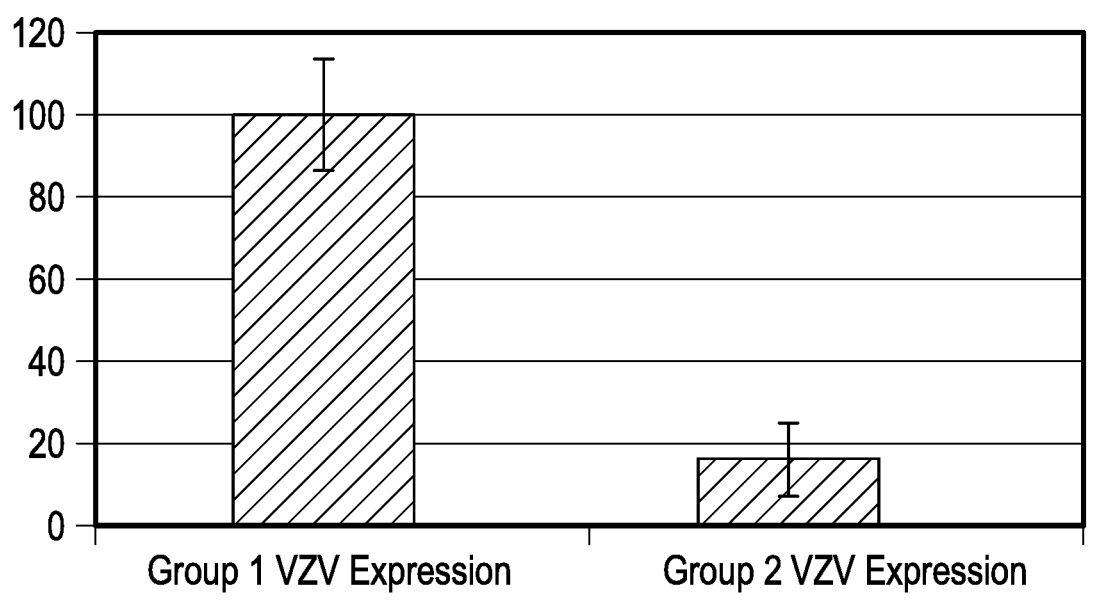

An in-vivo rodent study was conducted to ascertain treatment efficacy and safety of Formulation 1. Varicella zoster virus (VSV) was injected into the eyes of rodents and expression and symptoms of herpes zoster opthalmicus (HZO) was verified. Group 1 (ten subjects) of the subjects served as a control and received no treatment. Formulation 1 was administered topically to the eyes of group 2 (ten subjects) for seven days. At the conclusion of the seven day period, qPCR analysis was performed on samples taken from the eyes of group 1 and group 2 subjects in order to ascertain the amount of viral expression in the eyes of the two groups. As shown in Table 10 and FIG. 3, after the seven day administration period, the treatment group (group 2) exhibited less than 20% of the viral expression detected in the control group (group 1). Therefore, the subjects that were administered Formulation 1 exhibited over an 80% decrease in VSV expression as compared to the control group (group 1). The f-ratio value was 330.49151 while the p-value was <0.00001. Additional statistical analysis is shown in Table 11. Additionally, no adverse events occurred within the treatment population during administration of Formulation 1.

TABLE 10

Percentage of Viral Expression of
VSV After Seven Days (Example 12)

| Group 1 | Group 2 |
|---------|---------|
| 99.1    | 10.8    |
| 92.3    | 36.3    |
| 103.7   | 7.7     |
| 103.0

TABLE 10-continued

Percentage of Viral Expression of
VSV After Seven Days (Example 12)

| Group 1 | Group 2 |
|---------|---------|
| 84.0    | 11.1    |
| 91.9    | 12.5    |
| 115.8   | 7.7     |
| 118.7   | 12.4    |
| 86.6    | 19.4    |

TABLE 11

Statistical Analysis for Procedure of Example 12

|                    | Group 1 | Group 2  | Total     |
|--------------------|---------|----------|-----------|
| N                  | 10      | 10       | 20        |
| $\Sigma^x$         | 1000    | 161.6908 | 1161.6908 |
| Mean               | 100     | 16.1691  | 58.0845   |
| Standard Deviation | 11.5858 | 8.855    | 44.1599   |

Example 13. Preparation of Compositions Comprising Antiviral Agent

"Formulation 2" was prepared by mixing 49.8375 g of 0.9% w/v NaCl saline solution with 50.0 g of a 20% polihexanide biguanide, also known as poly(hexamethylenebiguanide) hydrochloride (PHMB), solution (Cosmocil CQ) to form a saline solution comprising the PHMB. A weighed amount of acyclovir was added to the saline solution. The resultant prepared saline solution comprising PHMB and acyclovir contained approximately 0.49% w/v NaCl (4.92 grams NaCl per 1000 mL H$_2$O), and 10% PHMB. Approximately 100 grams of saline solution comprising cationic biocides was heated to 122° F. and slowly added to approximately 1900 grams petrolatum heated to a temperature of 113° F. The heat was decreased slowly to between about 96° F. to about 104° F.

The resulting composition was shiny and white to slightly yellow in appearance. Specific gravity at 25° C. matches specification when it is from 0.830-0.910. Viscosity at @ 25° C. TF @ 10 rpm matches specification when it is from about 225,000-300,000 cps. The final formulation contained the following ingredients by weight percent: 92.5% petrolatum, 0.5% PHMB, 2.5 wt % acyclovir, and 4.49% saline solution.

Example 14. Topical Administration of Formulation 2 to the Ocular Region Improves Clinical Outcomes in Subjects Having Herpes Zoster Opthalmicus (HZO)

The effect of topical administration of Formulation 2 to the ocular region of human subjects having herpes zoster opthalmicus (HZO) will be studied using a randomized, double-blind clinical study. During the clinical study, a group of human subjects will be topically administered Formulation 2. In particular, Formulation 2 will be applied to the ocular region of a subject having or otherwise affected by the herpes zoster opthalmicus (HZO). Subjects receiving treatment using Formulation 2 are expected to have improved standard clinical outcomes. In particular, subjects receiving treatment according to the presently disclosed methods and techniques are expected to exhibit an improvement in one or more of the following clinical outcomes: reduction in eye redness or irritation, reduction in pain or discomfort, reduction in duration of presentation of herpes zoster opthalmicus (HZO), reduction or mitigation of symptoms associated with herpes zoster opthalmicus (HZO), reduction in blurred vision, and reduction in discharge from the eye. In some instances, the administration of acyclovir in Formulation 2 will be more effective in improving one or more clinical outcomes with respect to HZO than liquid formulations comprising acyclovir. In at least some instances, the administration of Formulation 2 will result in a greater improvement in one or more clinical outcomes with respect to HZO than administration of formulations comprising only PHMB (e.g., Formulation 1) or only acyclovir, thereby indicating a synergistic effect between the antiviral activity of PHMB and acyclovir when formulated in the presently disclosed petrolatum-based compositions.

Statements of the Present Disclosure

Numerous examples are provided herein to enhance understanding of the present disclosure. A specific set of statements are provided as follows.

Statement 1: A petrolatum-based composition comprising: petrolatum; and a saline solution comprising at least one cationic biocide.

Statement 2: A composition according to Statement 1, wherein the saline solution comprises sodium chloride dissolved in water.

Statement 3: A composition according to Statement 1 or Statement 2, wherein the saline solution comprises an aqueous 0.90% w/v sodium chloride solution.

Statement 4: A composition according to Statement 1 or Statement 2, wherein the saline solution comprises from about 0.20% to about 1.2% w/v sodium chloride.

Statement 5: A composition according to Statement 1 or Statement 2, wherein the saline solution comprises from about 0.40% to about 0.60% w/v sodium chloride.

Statement 6: A composition according to Statement 1 or Statement 2, wherein the saline solution comprises from about 0.40% to about 0.95% w/v sodium chloride.

Statement 7: A composition according to Statement 1 or Statement 2, wherein the saline solution comprises a sodium chloride solution having from about 2 g and about 12 g sodium chloride per liter water.

Statement 8: A composition according to Statement 1 or Statement 2, wherein the saline solution comprises from about 4 g to about 6 g sodium chloride per liter water.

Statement 9: A composition according to Statement 1 or Statement 2, wherein the saline solution comprises from about 4 g to about 9.5 g sodium chloride per liter water.

Statement 10: A composition according to any one of the preceding Statements 1-9, wherein the petrolatum-based composition comprises greater than about 80% by weight petrolatum.

Statement 11: A composition according to any one of the preceding Statements 1-9, wherein the petrolatum-based composition comprises greater than about 90% by weight petrolatum.

Statement 12: A composition according to any one of the preceding Statements 1-9, wherein the petrolatum-based composition comprises greater than about 95% by weight petrolatum.

Statement 13: A composition according to any one of the preceding Statements 1-12, wherein the petrolatum-based composition contains no emulsifier.

Statement 14: A composition according to any one of the preceding Statements 1-12, wherein the petrolatum-based composition excludes an added emulsifier.

Statement 15: A composition according to any one of the preceding Statements 1-14, wherein the saline solution is dispersed throughout the petrolatum.

Statement 16: A composition according to any one of the preceding Statements 1-15, wherein the saline solution is dispersed throughout the petrolatum in the form of nanodroplets, the nanodroplets characterized by an average diameter from about 10 nm to about 100 nm.

Statement 17: A composition according to any one of the preceding Statements 1-15, wherein the saline solution is dispersed throughout the petrolatum in the form of nanodroplets, the nanodroplets characterized by an average diameter from about 10 nm to about 500 nm.

Statement 18: A composition according to any one of the preceding Statements 1-15, wherein the saline solution is dispersed throughout the petrolatum in the form of nanodroplets, the nanodroplets characterized by an average diameter from about 10 nm to about 2000 nm.

Statement 19: A composition according to any one of the preceding Statements 1-18, wherein the cationic biocide is selected from the group consisting of benzalkonium chloride, cetrimide, chlorhexidine, polihexanide biguanide, and any combination thereof.

Statement 20: A composition according to any one of the preceding Statements 1-19, wherein the petrolatum-based composition comprises less than about 1% by weight cationic biocide.

Statement 21: A composition according to any one of the preceding Statements 1-20, wherein the cationic biocide is a mixture of benzalkonium chloride and polihexanide biguanide.

Statement 22: A composition according to any one of the preceding Statements 1-21, wherein the petrolatum-based composition comprises from about 0.1% to about 1% by weight polihexanide biguanide (PHMB).

Statement 23: A composition according to any one of the preceding Statements 1-21, wherein the petrolatum-based composition comprises from about 0.2% to about 0.6% by weight polihexanide biguanide (PHMB).

Statement 24: A composition according to any one of the preceding Statements 1-21, wherein the petrolatum-based composition comprises from about 0.3% to about 0.5% by weight polihexanide biguanide (PHMB).

Statement 25: A composition according to any one of the preceding Statements 1-24, wherein the petrolatum-based composition comprises from about 0.001% to about 0.01% by weight benzalkonium chloride (BZK).

Statement 26: A composition according to any one of the preceding Statements 1-24, wherein the petrolatum-based composition comprises from about 0.005% to about 0.007% by weight benzalkonium chloride (BZK).

Statement 27: A composition according to any one of the preceding Statements 1-26, wherein the petrolatum-based composition further comprises a compound that stimulates healing.

Statement 28: A composition according to Statement 27, wherein the composition that stimulates healing is selected from the group consisting of collagen and growth factors such as TGF-alpha, TGF-beta (TGFβ1, TGFβ2, TGFβ3), platelet-derived growth factor (PDGF), epidermal growth factor (EGF), fibroblast growth factor also referred to as keratinocyte growth factor (FGF1, FGF2, FGF4, FGF7), vascular endothelial growth factor (VEGF), insulin-like growth factor (IGF), connective tissue growth factor (CTGF), activin, interleukin-1 (IL1α, IL1β), TNFα, GM-CSF.

Statement 29: A process for preparing a petrolatum-based composition comprising petrolatum and a cationic biocide dissolved in a saline solution, the process comprising: a) preparing a saline solution, the saline solution comprising water, sodium chloride, and at least one cationic biocide; b) heating the petrolatum to a temperature sufficient to cause the petrolatum to melt to give a melted petrolatum and heating the saline solution to a temperature higher than the temperature of the melted petrolatum to give a heated saline solution; c) mixing the melted petrolatum and the heated saline solution to give a melted mixture; and d) cooling the melted mixture to give the petrolatum-based composition.

Statement 30: The process according to Statement 29, wherein an emulsifier is not used.

Statement 31: The process according to Statement 29 or Statement 30, wherein the heated saline solution has a temperature that is about 1° C. to about 10° C. higher than the temperature of the melted petrolatum.

Statement 32: The process according to any one of Statements 29-31, wherein the heated saline solution has a temperature that is about 1° C. to about 5° C. higher than the temperature of the melted petrolatum.

Statement 33: The process according to any one of Statements 29-32, wherein the preparing a saline solution comprises mixing one or more aqueous solutions comprising at least one cationic biocide with an initial saline solution.

Statement 34: The process according to any one of Statements 29-33, wherein the preparing a saline solution comprises mixing an aqueous solution comprising benzalkonium chloride (BZK), an aqueous solution comprising polihexanide biguanide (PHMB), and an initial saline solution.

Statement 35: The process according to any one of Statements 29-34, wherein the saline solution comprises sodium chloride dissolved in water.

Statement 36: The process according to any one of Statements 29-35, wherein the initial saline solution comprises an aqueous 0.90% w/v sodium chloride solution.

Statement 37: The process according to any one of Statements 29-36, wherein the saline solution comprises from about 0.20% to about 1.2% w/v sodium chloride.

Statement 38: The process according to any one of Statements 29-36, wherein the saline solution comprises from about 0.40% to about 0.60% w/v sodium chloride.

Statement 39: The process according to any one of Statements 29-36, wherein the saline solution comprises from about 0.40% to about 0.95% w/v sodium chloride.

Statement 40: The process according to any one of Statements 29-36, wherein the saline solution comprises a sodium chloride solution having from about 2 g and about 12 g sodium chloride per liter water.

Statement 41: The process according to any one of Statements 29-36, wherein the saline solution comprises from about 4 g to about 6 g sodium chloride per liter water.

Statement 42: The process according to any one of Statements 29-36, wherein the saline solution comprises from about 4 g to about 9.5 g sodium chloride per liter water.

Statement 43: The process according to any one of Statements 29-42, wherein the petrolatum-based composition comprises greater than about 80% by weight petrolatum.

Statement 44: The process according to any one of Statements 29-42, wherein the petrolatum-based composition comprises greater than about 90% by weight petrolatum.

Statement 45: The process according to any one of Statements 29-42, wherein the petrolatum-based composition comprises greater than about 95% by weight petrolatum.

Statement 46: The process according to any one of Statements 29-45, wherein the cationic biocide is selected from the group consisting of benzalkonium chloride, cetrimide, chlorhexidine, and polihexanide biguanide.

Statement 47: The process according to any one of Statements 29-45, wherein the cationic biocide is a mixture of benzalkonium chloride and polihexanide biguanide.

Statement 48: A method for treating or preventing an ocular disease in an eye of a patient in need thereof, the method comprising topical administration to the ocular region of the patient a therapeutically effective amount of a petrolatum-based composition according to any one of the Statements 1-28 and 67-70.

Statement 49: A method for treating or preventing an ocular infection in an eye of a patient in need thereof, the method comprising topical administration to the ocular region of the patient a therapeutically effective amount of a petrolatum-based composition according to any one of the Statements 1-28 and 67-70.

Statement 50: The method according to Statement 48 or Statement 49, wherein the ocular disease or ocular infection is selected from the group consisting of conjunctivitis, keratitis, blepharitis, vitritis, uveitis, chorioretinitis, neuroretinitis, and trachoma.

Statement 51: The method according to Statement 48 or Statement 49, wherein the ocular disease or ocular infection is selected from the group consisting of herpes zoster opthalmicus (HZO), bacterial conjunctivitis, viral conjunctivitis, bacterial keratitis, viral keratitis, fungal keratitis, acanthamoebic keratitis, bacterial blepharitis, viral blepharitis, trachoma, ocular histoplasmosis syndrome, and onchocerciasis.

Statement 52: The method according to Statement 49, wherein the ocular infection is a fungal infection.

Statement 53: The method according to Statement 49, wherein the ocular infection is an amoeba infection.

Statement 54: The method according to Statement 49, wherein the ocular infection is a viral infection.

Statement 55: The method according to Statement 49, wherein the ocular infection is a bacterial infection.

Statement 56: A method for treating or preventing an ocular disease in an eye of a patient in need thereof, the method comprising topical administration to the ocular region of the patient a therapeutically effective amount of a petrolatum-based composition prepared according to the process of any one of the Statements 29-47 and 71-74.

Statement 57: A method for treating or preventing an ocular infection in an eye of a patient in need thereof, the method comprising topical administration to the ocular region of the patient a therapeutically effective amount of a petrolatum-based composition prepared according to the process of any one of the Statements 29-47 and 71-74.

Statement 58: The method according to Statement 56 or Statement 57, wherein the ocular disease or ocular infection is selected from the group consisting of conjunctivitis, keratitis, blepharitis, vitritis, uveitis, chorioretinitis, neuroretinitis, and trachoma.

Statement 59: The method according to Statement 56 or Statement 57, wherein the ocular disease or ocular infection is selected from the group consisting of herpes zoster opthalmicus (HZO), bacterial conjunctivitis, viral conjunctivitis, bacterial keratitis, viral keratitis, fungal keratitis, acanthamoebic keratitis, bacterial blepharitis, viral blepharitis, trachoma, ocular histoplasmosis syndrome, and onchocerciasis.

Statement 60: The method according to Statement 57, wherein the ocular infection is a fungal infection.

Statement 61: The method according to Statement 57, wherein the ocular infection is an amoeba infection.

Statement 62: The method according to Statement 57, wherein the ocular infection is a viral infection.

Statement 63: The method according to Statement 57, wherein the ocular infection is a bacterial infection.

Statement 64: A method of treating or preventing shingles in an eye of a patient in need thereof, the method comprising topical administration to the eye or ocular region of the patient a therapeutically effective amount of a petrolatum-based composition according to any one of the Statements 1-28 and 67-70.

Statement 65: A method of treating or preventing herpes zoster opthalmicus (HZO) in an eye of a patient in need thereof, the method comprising topical administration to the eye or ocular region of the patient a therapeutically effective amount of a petrolatum-based composition according to any one of Statements 1-28 and 67-70.

Statement 66: A method of treating or preventing a varicella zoster virus (VSV) infection in an eye of a patient in need thereof, the method comprising topical administration to the eye or ocular region of the patient a therapeutically effective amount of a petrolatum-based composition according to any one of Statements 1-28 and 67-70.

Statement 67: The composition according to any one of Statements 1-28 and 67-70, further comprising an antiviral agent.

Statement 68: The composition according to Statement 67, wherein the antiviral agent is selected from the group consisting of acyclovir, valacyclovir, and famciclovir.

Statement 69: The composition according to Statement 67 or Statement 68, wherein the antiviral agent comprises from about 0.5 wt % to about 5.0 wt % of the petrolatum-based composition.

Statement 70: The composition according to any one of Statements 67-69, wherein the antiviral agent is acyclovir, the acyclovir comprising from about 0.5 wt % to about 5.0 wt % of the petrolatum-based composition.

Statement 71: The process according to any one of Statements 29-47, wherein the saline solution further comprises an antiviral agent.

Statement 72: The process according to Statement 71, wherein the antiviral agent is selected from the group consisting of acyclovir, valacyclovir, and famciclovir.

Statement 73: The process according to Statement 71 or Statement 72, wherein the antiviral agent comprises from about 0.5 wt % to about 5.0 wt % of the petrolatum-based composition.

Statement 74: The process according to any one of the preceding Statements 71-73, wherein the antiviral agent is acyclovir, the acyclovir comprising from about 0.5 wt % to about 5.0 wt % of the petrolatum-based composition.

What is claimed is:

1. A method for treating or preventing an ocular disease in an eye of a patient in need thereof, the method comprising topical administration to the ocular region of the patient a therapeutically effective amount of a petrolatum-based composition, the petrolatum-based composition comprising:
   petrolatum; and
   a saline solution comprising polihexanide biguanide (PHMB), wherein the petrolatum-based composition comprises greater than about 80% by weight petrolatum; and wherein the ocular disease is selected from the group consisting of herpes zoster opthalmicus (HZO), bacterial conjunctivitis, viral conjunctivitis, bacterial keratitis, viral keratitis, fungal keratitis, acanthamoebic keratitis, bacterial blepharitis, viral blepharitis, trachoma, ocular histoplasmosis syndrome, and onchocerciasis, conjunctivitis, keratitis, blepharitis, vitritis, uveitis, chorioretinitis, neuroretinitis, and trachoma.

2. The method according to claim 1, wherein the saline solution comprises from about 0.20% to about 1.2% w/v sodium chloride.

3. The method according to claim 1, wherein the petrolatum-based composition comprises from about 0.1% to about 1% by weight polihexanide biguanide (PHMB).

4. The method according to claim 1, wherein the petrolatum-based composition further comprises an antiviral agent selected from the group consisting of acyclovir, valacyclovir, and famciclovir.

5. The method according to claim 4, wherein the antiviral agent comprises from about 0.5 wt % to about 5.0 wt % of the petrolatum-based composition.

6. The method according to claim 3, wherein the petrolatum-based composition further comprises from about 0.5 wt % to about 5.0 wt % acyclovir.

7. The method according to claim 6, wherein the petrolatum-based composition contains no emulsifier.

8. The method according to claim 5, wherein the petrolatum-based composition excludes an added emulsifier beyond the recited components.

9. A method of treating or preventing herpes zoster opthalmicus (HZO) in an eye of a patient in need thereof, the method comprising topical administration to the ocular region of the patient a therapeutically effective amount of a petrolatum-based composition, the petrolatum-based composition comprising:

petrolatum; and a saline solution comprising polihexanide biguanide (PHMB), wherein the petrolatum-based composition comprises greater than about 80% by weight petrolatum.

10. The method according to claim 9, wherein the saline solution comprises from about 0.20% to about 1.2% w/v sodium chloride.

11. The method according to claim 9, wherein the petrolatum-based composition comprises from about 0.1% to about 1% by weight polihexanide biguanide (PHMB).

12. The method according to claim 9, wherein the petrolatum-based composition further comprises an antiviral agent selected from the group consisting of acyclovir, valacyclovir, and famciclovir.

13. The method according to claim 12, wherein the antiviral agent comprises from about 0.5 wt % to about 5.0 wt % of the petrolatum-based composition.

14. The method according to claim 9, wherein the petrolatum-based composition comprises from about 0.5 wt % to about 5.0 wt % acyclovir.

* * * * *